United States Patent [19]

Shin

[11] Patent Number: 4,636,574

[45] Date of Patent: Jan. 13, 1987

[54] PROCESS FOR PREPARING ARYLISOTHIOCYANATES

[75] Inventor: Kju H. Shin, Baton Rouge, La.

[73] Assignee: Ethyl Corporation, Richmond, Va.

[21] Appl. No.: 794,855

[22] Filed: Nov. 4, 1985

[51] Int. Cl.$^4$ ............................................. C07C 161/04
[52] U.S. Cl. ..................................... 558/18; 546/232
[58] Field of Search ........................... 558/18; 546/232

[56] References Cited

U.S. PATENT DOCUMENTS 3,322,810  5/1967  Olin .................................... 558/18 X

OTHER PUBLICATIONS

Barton, *Comprehensive Organic Chemistry*, vol. 3, pp. 461–465 (1979).
Molina et al., *Synthesis*, pp. 596–597 (1982).

*Primary Examiner*—Dolph H. Torrence
*Attorney, Agent, or Firm*—Donald L. Johnson; John F. Sieberth; Patricia J. Hogan

[57] ABSTRACT

Arylisothiocyanates are prepared by reacting a primary arylamine with carbon disulfide in the presence of a tertiary amine.

7 Claims, No Drawings

PROCESS FOR PREPARING ARYLISOTHIOCYANATES

FIELD OF INVENTION

This invention relates to arylisothiocyanates and more particularly to a process for preparing them.

BACKGROUND

Arylisothiocyanates are known to be useful in a variety of applications, such as applications requiring biological activity. They are most commonly prepared by the reaction of an appropriate primary amine with thiophosgene, and they can also be synthesized by other known techniques, such as those taught in D. H. Barton, *Comprehensive Organic Chemistry*, Vol. 3, Pergamon (Elmsford, N.Y.), 1979, pp. 461-465, and in Molina et al., *Synthesis*, 1982, pp. 596-597. However, there is a need for a more economical synthesis.

SUMMARY OF INVENTION

An object of this invention is to provide a novel process for preparing arylisothiocyanates.

Another object is to provide such a process which is economical.

These and other objects are attained by reacting a primary arylamine with carbon disulfide in the presence of a tertiary amine.

DETAILED DESCRIPTION

The primary arylamine employed in the practice of the invention may be any primary arylamine which is free of substituents that would interfere with the reaction, i.e., any aromatic compound wherein the aromatic ring bears either no substituents or only inert substituents in addition to the required primary amino group. Such compounds include, e.g., alpha-naphthylamine; beta-naphthylamine; aniline; anilines bearing a substituent such as chloro, methoxy, phenoxy, etc., in the 2- or 4-position; anilines bearing a hydrocarbyl substituent such as methyl, ethyl, isopropyl, butyl, etc., in the 4-position; 3-nitroaniline; 2,4-dihaloanilines; and the like. However, the arylamines which appear to be most readily reacted in the process are the anilines which bear a hydrocarbyl substituent in one or both of the positions ortho to the amino group. Exemplary of these more reactive arylamines are the 2-benzyl-, cylcohexyl-, methyl-, ethyl-, isopropyl, sec-butyl-, and t-butylanilines; the 2,4- and 2,6-dimethyl-, diethyl-, diisopropyl-, di-sec-butyl-, and di-t-butylanilines; 2-methyl-6-ethylaniline; 2-methyl-6-isopropylaniline; 2-ethyl-6-isopropylaniline; 2-isopropyl-4-methylaniline; 2-ethyl-4-methylaniline; the 2,6-dimethyl-, diisopropyl, and di-t-butyl-4-dimethylaminomethylanilines; the corresponding 2,6-dialkylanilines having a piperidylmethyl group in the 4-position, etc.

In a preferred embodiment of the invention, the primary arylamine is an alkylated aniline bearing at least one alkyl group of 1-6 carbons in an ortho position and optionally bearing a tertiary aminomethyl group, such as dimethylaminomethyl, diethylaminomethyl, piperidylmethyl, etc., in an ortho or para position. The compounds containing a tertiary aminomethyl group are of particular interest in that they have the tertiary amine catalyst built into their molecules, thus obviating or reducing the need for a separate compound to serve as a catalyst.

The amount of carbon disulfide reacted with the primary arylamine should be at least the stoichiometric amount and—especially when the reaction is conducted at atmospheric pressure—is preferably an excess, e.g., about 5-25 mols of carbon disulfide per mol of arylamine. There does not appear to be any maximum to the amount that may be employed.

The tertiary amine employed as a catalyst may be any tertiary amine, i.e., a compound in which all valences of the amino nitrogen are satisfied by carbons of alkyl, cycloalkyl, and/or aryl groups and/or of a heterocyclic ring. As mentioned above, it may be the primary arylamine itself when the arylamine bears a tertiary amino substituent. Exemplary of other tertiary amines that may be employed are trimethylamine, triethylamine, tripropylamine, higher trialkylamines, especially those containing up to 6 carbons, triphenylamine, pyridine, 1,8-diazabicyclo[5.4.0]undec-7-ene, etc. The tertiary amine is used in catalytic amounts, generally about 0.3-2 mols per mol of the primary arylamine, the specific amount most desirably employed varying with factors such as the strength of the tertiary amine, the reactivity of the primary arylamine, and the temperature employed.

The reaction is conducted by mixing the primary arylamine, carbon disulfide, and tertiary amine in a suitable solvent, preferably an alcohol such as methanol, ethanol, isopropanol, t-butanol, etc., and heating the reaction mixture at a suitable temperature, preferably reflux temperature, to effect reaction. In a preferred embodiment of the invention, the reaction is conducted under pressure to permit the use of temperatures higher than can otherwise be employed. Thus, the reaction is generally conducted under a pressure of about 1-1000 psi, preferably about 500 psi, at a temperature of about 40°-250° C., preferably about 150° C. The use of a pressure distillation device is desirable to contain the carbon disulfide and vent the hydrogen sulfide formed by the reaction.

The following examples are given to illustrate the invention and are not intended as a limitation thereof.

EXAMPLE I

Part A

A mixture of one molar proportion of 2,6-diisopropylaniline (DIA) and 1.6 molar proportions of carbon disulfide in 4.4 molar proportions of ethanol was refluxed for 1.5 hours, after which GC analysis showed a DIA/2,6-diisopropylphenylisothiocyanate (DIPI) area % ratio of 5.3/1. The reaction was continued for another 55 hours during which another 7 molar proportions of carbon disulfide were added incrementally. At this point the DIA/DIPI ratio was 1/1.7.

Part B

Triethylamine (0.3 molar proportion) was added to the reaction mixture, and the reaction was continued for another 17 hours, at which time the DIA/DIPI ratio was determined to be 1/8.9. Then another 0.3 molar proportion of triethylamine was added and reaction continued for 6.5 hours to form a final reaction mixture in which the DIA/DIPI ratio was 1/9.4. Essentially no other products were formed, and the identity of the product was confirmed by GC-MS. After workup, essentially pure DIPI was obtained in a yield of 74%.

EXAMPLE II

A mixture of one molar proportion of 4-piperidylmethyl-2,6-diisopropylaniline (PMDIA) and 1.2 molar proportions of carbon disulfide in 19.5 molar proportions of ethanol was refluxed under a nitrogen atmosphere for one hour, after which GC analysis showed that the PMDIA/4-piperidylmethyl-2,6-diisopropylphenylisothiocyanate (PMDIPI) area % ratio was about 1/1. After the addition of another 1.2 molar proportions of carbon disulfide and continuation of the reaction for another two hours and 20 minutes, the PMDIA/PMDIPI ratio was determined to be 1/3.9. The reaction was continued for another 24 hours during which 4.5 molar proportions of carbon disulfide were added incrementally to form a final reaction mixture in which the PMDIA/PMDIPI ratio was 1/19.5. There was very little by-product.

EXAMPLE III

Part A

A mixture of one molar proportion of 2-ethylaniline (EA) and 11.8 molar proportions of carbon disulfide in 4.3 molar proportions of ethanol was refluxed for about 16 hours, after which GC analysis showed that only a trace of the desired 2-ethylphenylisothiocyanate (EPI) had been formed to provide an EA/EPI area % ratio of 25/1.

Part B

Triethylamine (0.9 molar proportion) was added and reflux continued for 35 minutes, at which point the EA/EPI ratio was 1/1. After another four hours and 10 minutes, the ratio was 1/1.98.

EXAMPLE IV

A mixture of one molar proportion of EA, 2.5 molar proportions of carbon disulfide, and 1.3 molar proportions of pyridine in 8.5 molar proportions of ethanol was refluxed for three hours, after which the EA/EPI ratio was 2.9/1. During the following 24 hours, an additional 1.3 molar proportions of pyridine and an additional 11 molar proportions of carbon disulfide were added, and the reaction was continued for about 20 more hours. The EA/EPI ratio in the final reaction mixture was 1/1.44.

EXAMPLE V

A mixture of one molar proportion of EA, 3.1 molar proportions of carbon disulfide, and 0.2 molar proportion of triethylenediamine in 8.5 molar proportions of ethanol was refluxed for two hours, after which the EA/EPI ratio was 1.2/1. Reaction was continued for another 42–43 hours, during which another 0.3 molar proportion of triethylenediamine and another 2.7 molar proportions of carbon disulfide were added. The EA/EPI ratio in the final reaction mixture was 1/2.3.

EXAMPLE VI

A mixture of one molar proportion of EA, 7 molar proportions of carbon disulfide, and one molar proportion of 1,8-diazabicyclo[5.4.0]undec-7-ene (DBU) in 11.4 molar proportions of ethanol was refluxed for two hours, after which the EA/EPI ratio was 1/1.1. After the addition of another 7 molar proportions of carbon disulfide, the reaction was continued for 8 hours, another 7 molar proportions of carbon disulfide and another molar proportion of DBU were added, and reaction was continued for another two hours. The EA/EPI ratio in the reaction mixture was 1/2.4.

It is obvious that many variations can be made in the products and processes set forth above without departing from the spirit and scope of this invention.

What is claimed is:

1. A process which comprises reacting a primary arylamine with carbon disulfide in the presence of a tertiary amine so as to prepare an arylisothiocyanate.
2. The process of claim 1 wherein the primary arylamine is an aniline.
3. The process of claim 2 wherein the aniline bears a hydrocarbyl substituent in an ortho position.
4. The process of claim 3 wherein the hydrocarbyl substituent is an alkyl group containing 1–6 carbons.
5. The process of claim 1 wherein the tertiary amine is a tertiary aminomethyl substituent on the aromatic ring of the primary arylamine.
6. The process of claim 1 wherein the tertiary amine is a trialkylamine.
7. The process of claim 1 wherein the tertiary amine is 1,8-diazadicyclo[5.4.0]undec-7-ene.

* * * * *